US008883087B2

(12) United States Patent
Hamamoto et al.

(10) Patent No.: US 8,883,087 B2
(45) Date of Patent: Nov. 11, 2014

(54) BIOLOGICAL SAMPLE MEASUREMENT APPARATUS

(75) Inventors: Hiroyuki Hamamoto, Ehime (JP); Akio Nagao, Kagawa (JP); Masumi Aono, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 14/000,729

(22) PCT Filed: Feb. 28, 2012

(86) PCT No.: PCT/JP2012/001340
§ 371 (c)(1),
(2), (4) Date: Aug. 21, 2013

(87) PCT Pub. No.: WO2012/120829
PCT Pub. Date: Sep. 13, 2012

(65) Prior Publication Data
US 2013/0323124 A1 Dec. 5, 2013

(30) Foreign Application Priority Data

Mar. 4, 2011 (JP) ................. 2011-047333
Mar. 31, 2011 (JP) ................. 2011-077621
Nov. 30, 2011 (JP) ................. 2011-261410

(51) Int. Cl.
| G01N 33/00 | (2006.01) |
| G01N 21/01 | (2006.01) |
| A61B 5/151 | (2006.01) |
| A61B 5/15 | (2006.01) |
| G01N 21/84 | (2006.01) |
| G01N 33/66 | (2006.01) |
| A61B 5/145 | (2006.01) |

(52) U.S. Cl.
CPC .......... *G01N 33/66* (2013.01); *G01N 2201/022* (2013.01); *G01N 21/01* (2013.01); *A61B 5/151* (2013.01); *A61B 5/1411* (2013.01); *G01N 21/8483* (2013.01); *A61B 5/150305* (2013.01); *A61B 5/150022* (2013.01); *A61B 5/14532* (2013.01)

USPC ............ 422/404; 455/50; 455/401; 455/560; 455/561

(58) Field of Classification Search
USPC ............................ 422/404, 50, 401, 560, 561
See application file for complete search history.

(56) References Cited

U.S. PATENT DOCUMENTS 6,781,522 B2 * 8/2004 Sleva et al. ................. 340/870.1
2011/0218502 A1 9/2011 Iio et al.

FOREIGN PATENT DOCUMENTS

| JP | 2009-262951 A | 11/2009 |
| JP | 2010-136594 A | 6/2010 |
| WO | 2010/055608 A1 | 5/2010 |

OTHER PUBLICATIONS

International Search Report for PCT/JP2012/001340 dated Jun. 5, 2012.

*Primary Examiner* — Sam P Siefke
(74) *Attorney, Agent, or Firm* — Pearne & Gordon LLP

(57) ABSTRACT

A biological sample measurement apparatus includes container (10) having an opening in a top surface thereof and right and left accommodation chambers (12) and (13) formed by separating an inner space and the opening in container (10) by partition wall (11a), measurement device (1) accommodated in accommodation chamber (12) of container (10), and a holder accommodated in accommodation chamber (13) of container (10) and holding measurement device (1). Provided are recesses (15, 16) configuring holding means holding measurement device (1) on an outer peripheral wall configuring accommodation chamber (12) or in accommodation chamber (12) in a state where sensor mounting section (4) of measurement device (1) is projected to an outside of accommodation chamber (12).

13 Claims, 13 Drawing Sheets

BIOLOGICAL SAMPLE MEASUREMENT APPARATUS

TECHNICAL FIELD

The present invention relates to a biological sample measurement apparatus which measures biological information, such as a blood sugar level, from blood.

BACKGROUND ART

Conventionally such a biological sample measurement apparatus includes a biological sample measurement device, and a holder holding the biological sample measurement device.

That is, when not used, the biological sample measurement device is held on the holder to be charged (for instance, see Patent Literature 1).

In the conventional example, the biological sample measurement device and the holder are packed in different packing materials in a manufacturing factory to be conveyed to a conveyance destination (e.g., a hospital, and a home). Then, at the conveyance destination, the packing materials are removed to be discharged as garbage.

That is, the packing materials which are articles to be conveyed are unnecessary and discharged after conveyance. The packing materials thus have low convenience.

Accordingly, an object of the present invention is to use an article to be conveyed for a biological sample measurement device and a holder to enhance convenience.

CITATION LIST

Patent Literature

PTL 1: Unexamined Japanese Patent Publication No, 2010-136594

SUMMARY OF THE INVENTION

To achieve this object, the present invention provides a biological sample measurement apparatus including a container having an opening in a top surface thereof and first and second accommodation chambers formed by separating an inner space and the opening in the container by a partition wall, the biological sample measurement device accommodated in the first accommodation chamber of the container, and a holder accommodated in the second accommodation chamber of the container for holding the biological sample measurement device. The biological sample measurement apparatus further includes holding means holding the biological sample measurement device on an outer peripheral wall configuring the first accommodation chamber or in the first accommodation chamber in a state where a sensor mounting section of the biological sample measurement device is projected to an outside of the first accommodation chamber. In addition, a rotation shaft is projected downward from the bottom of the first accommodation chamber. This can achieve the predetermined object.

DESCRIPTION OF EMBODIMENTS

Hereinafter, exemplary embodiments of the present invention will be described with reference to the accompanying drawings.

First Exemplary Embodiment

Figure 1:
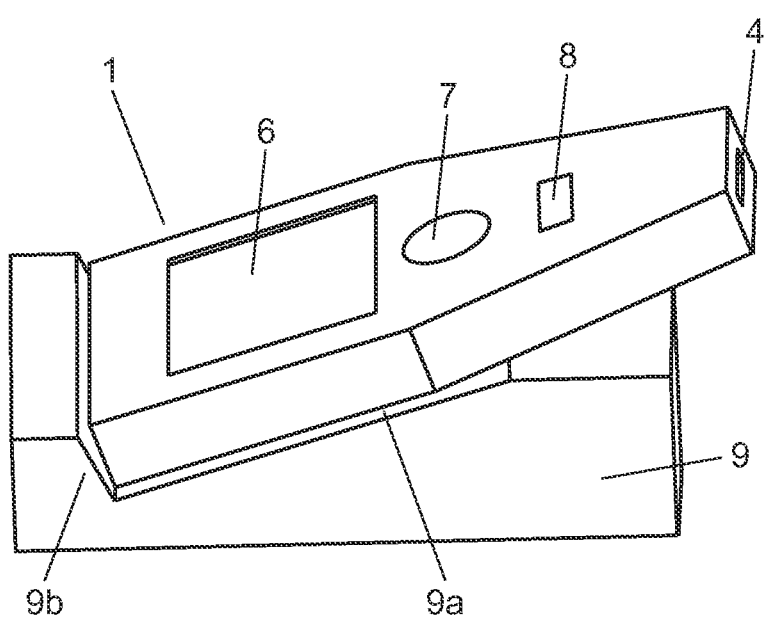
FIG. 1 is a perspective view of a biological sample measurement device and a holder configuring the biological sample measurement apparatus according to a first exemplary embodiment of the present invention.
Figure 2:
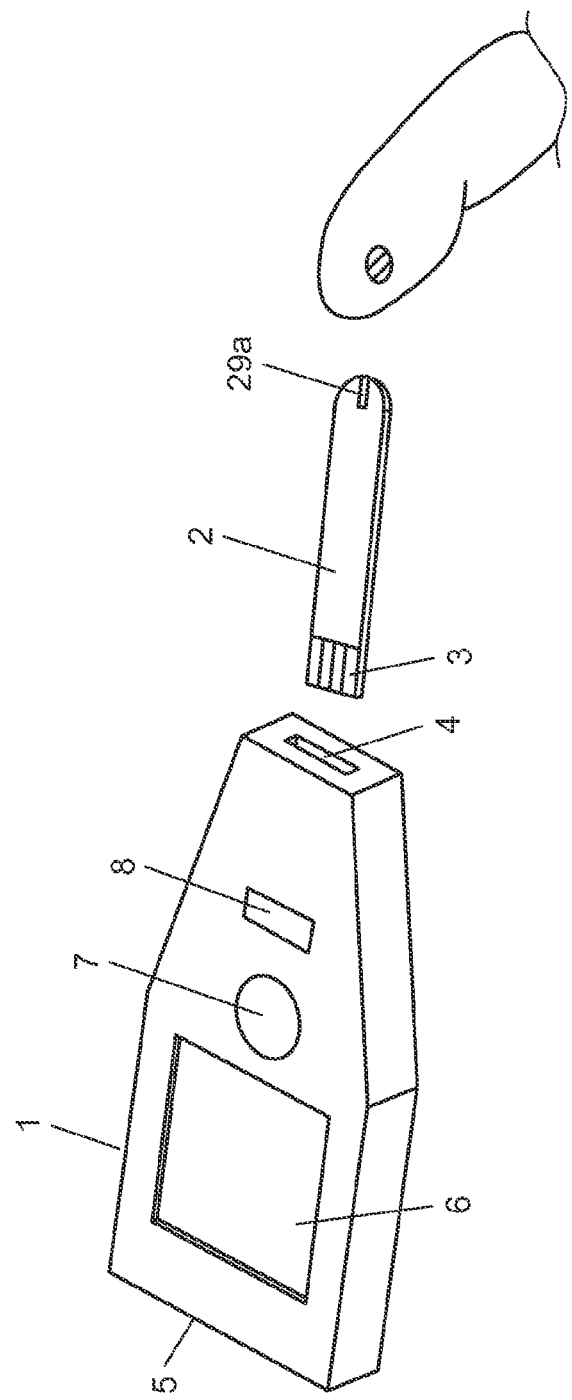
FIG. 2 is a perspective view of the biological sample measurement device configuring the biological sample measurement apparatus according to the first exemplary embodiment of the present invention at the time of use.

As shown in FIG. 1, blood sugar level measurement device 1 (an example of a biological sample measurement device)

used iii e.g., a hospital is formed into a substantially rectangular parallelepiped shape. As shown in FIG. 2, sensor mounting section 4 is provided on a side surface on one end side of measurement device 1 in a longitudinal direction, and inserts thereinto connection terminal 3 of blood sugar level sensor (an example of a biological sample detection sensor) 2. The one end side is a biological sample measurement side.

Laser scanner unit (an example of an optical information reading unit) 5 is provided on the other end side of measurement device 1, and reads ID information of a measuring person and a patient. The other end side is an formation reading side.

A width of measurement device 1 is gradually decreased from a center to the one end side thereof in the longitudinal direction. With this configuration, a width on the one end side orthogonal to the longitudinal direction is smaller than a width on the other end side orthogonal to the longitudinal direction.

On a top surface of measurement device 1, provided are display unit 6, scanner button 7 driving scanner unit 5, and power source button 8.

As shown in FIG. 1, when not used, measurement device 1 is held on holding portion 9a of holder 9. As shown in FIG. 1, holding portion 9a is tilted downward from a front end thereof to a rear end thereof. Stopper 9b is provided on a lower end side of tilting, and receives measurement device 1 lowered according to the tilting of holding portion 9a. Holder 9 can also be used as an electric charger for measurement device 1.

Figure 3:
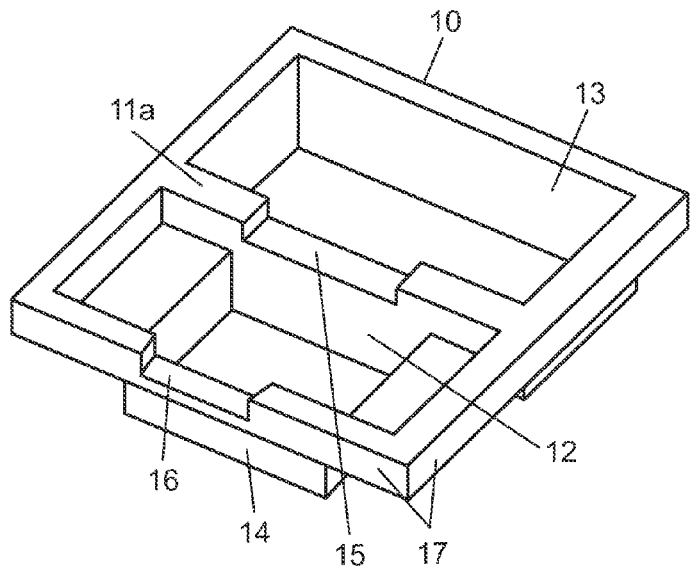
FIG. 3 is a perspective view of a container configuring the biological sample measurement apparatus according to the first exemplary embodiment of the present invention, seen from above.

FIG. 3 is a diagram showing container 10 accommodating measurement device 1 and holder 9 therein. Container 10 has an opening in a top surface thereof, and accommodation chamber 12 (first accommodation chamber) and accommodation chamber 13 (second accommodation chamber) formed by separating an inner space and the opening in container 10 to right and left by partition wall 11a. Each of accommodation chambers 12 and 13 has a rectangular parallelepiped shape so that a top surface thereof is rectangularly opened. Rectangular parallelepiped recess 14 is projected downward from a bottom at a center of accommodation chamber 12. A bottom of recess 14 and a bottom of accommodation chamber 13 are planar, and are substantially flush with each other.

Further, in accommodation chamber 12 of this exemplary embodiment, recess 15 is a first recess formed at a center in a top surface of partition wall 11a as a side wall of accommodation chamber 12 and configuring holding means holding measurement device 1, and recess 16 is a second recess formed at a center in a top surface of a side wall of accommodation chamber 12 opposite to recess 15 (that is, an outer peripheral wall of container 10) and configuring holding means holding measurement device 1. Recesses 15 and 16 are used when measurement device 1 is taken out from container 10, and are also used at the time of measurement of measurement device 1, that is, at the time of actual use of measurement device 1. The detail thereof will be described later.

Furthermore, in this exemplary embodiment, container 10 is formed of a resilient resin (e.g., polypropylene). As shown in FIG. 3, folding portion 17 is provided on an overall periphery of the top surface of container 10 so that ends thereof are folded downward. An outer peripheral strength of container 10 can thus be enhanced. Container 10 can be conveyed by holding folding portion 17.

Figure 4:
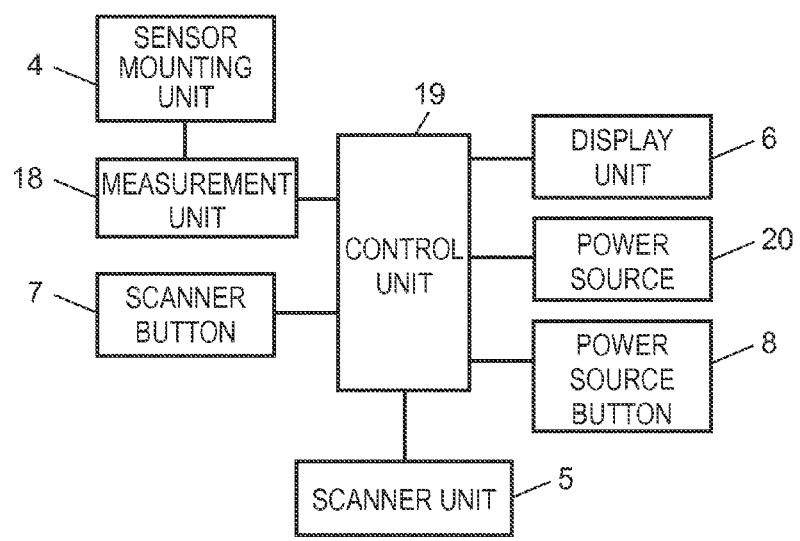
FIG. 4 is a control block diagram of the biological sample measurement device configuring the biological sample measurement apparatus according to the first exemplary embodiment of the present invention.

FIG. 4 shows a control block diagram of measurement device 1. Measurement unit 18 to which sensor mounting section 4 is connected is connected to control unit 19. To control unit 19, connected are display unit 6 displaying a blood sugar level measured by measurement unit 18, scanner unit 5, scanner button 7, power source button 8, and power source 20.

That is, in blood sugar level measurement, when a user presses power source button 8, power source 20 supplies electricity to control unit 19 and scanner unit 5. When the user then presses scanner button 7, scanner unit 5 reads ID information of a measuring person and a patient and ID information of bottle case 22 (shown in FIG. 7) accommodating blood sugar level sensor 2 therein via e.g., a barcode.

Thereafter, connection terminal 3 of blood sugar level sensor 2 is mounted on sensor mounting section 4. In that state, blood is spotted onto spotting unit 29a (shown in FIG. 2) on one end side of blood sugar level sensor 2. A blood sugar level is then measured by measurement unit 18 to be displayed on display unit 6.

In the above configuration, features of the biological sample measurement apparatus according to this exemplary embodiment will be described below with reference to FIGS. 5 to 7.

First, a state of the biological sample measurement apparatus according to this exemplary embodiment at the time of conveyance will be described with reference to FIG. 5.

Figure 5:
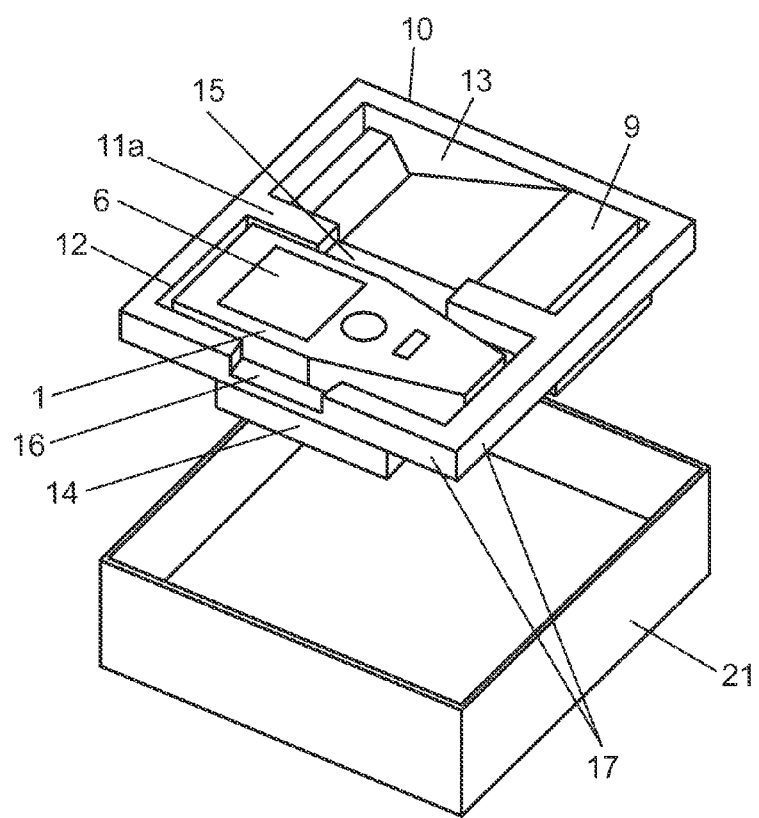
FIG. 5 is a perspective view of the biological sample measurement apparatus according to the first exemplary embodiment of the present invention at the time of conveyance.

As shown in FIG. 5, at the time of conveyance of the biological sample measurement apparatus according to this exemplary embodiment, in a manufacturing factory, measurement device 1 is accommodated in accommodation chamber 12 of container 10, and holder 9 is accommodated in accommodation chamber 13 of container 10. Thereafter, measurement device 1 and holder 9 are integrally packed in container 10 to be conveyed to a conveyance destination (e.g., a hospital, and a home).

Recess 14 at the bottom of accommodation chamber 12 is formed of a resilient resin (e.g., polypropylene). Vibration with respect to measurement device 1 at the time of conveyance can be effectively prevented.

The bottom of accommodation chamber 13 and the bottom of recess 14 of accommodation chamber 12, which are substantially flush with each other, are abutted onto a bottom of box 21 at the time of conveyance. Further, folding portion 17 provided on the overall outer periphery in an upper portion of container 10 is abutted onto an upper portion of box 21. Container 10 can thus be conveyed to be tightly held in box 21. FIG. 5 shows only box 21 in which an upper surface thereof is opened, but, of course, a box in which a lower surface thereof is opened (not shown) covers an outer periphery of box 21 from above. Upper and lower boxes 21 thus cover container 10.

That is, container 10 can be used as a conveying material at the time of conveyance.

Figure 6:
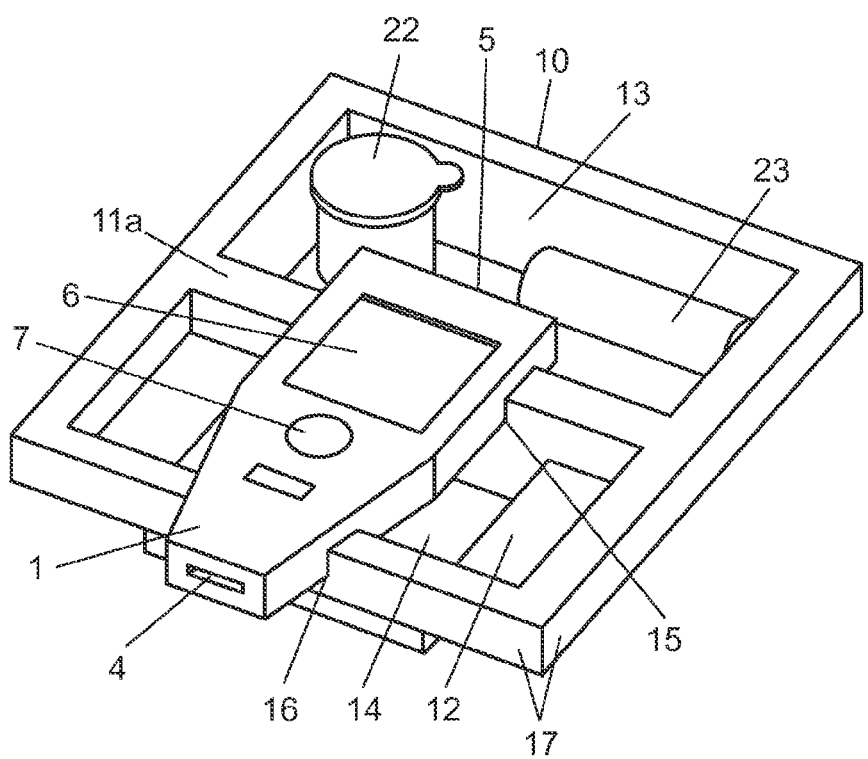
FIG. 6 is a perspective view of the container and the biological sample measurement device configuring the biological sample measurement apparatus according to the first exemplary embodiment of the present invention at the time of use.

When container 10 reaches a conveyance destination (e.g., a hospital, and a home), the upper box (not shown) is opened, and then, as shown in FIGS. 5 and 6, container 10 is taken out from box 21. Thereafter, holder 9 is taken out from accommodation chamber 13 of container 10, and is installed in a charging place for measurement device 1.

When holder 9 is taken out from accommodation chamber 13 in this manner, as seen from FIG. 5, the user holds side portions at the center of measurement device 1 between his/her fingers by using two recesses 15 and 16 to vertically lift measurement device 1. Measurement device 1 can thus be easily taken up from accommodation chamber 12. As shown in FIG. 1, measurement device 1 is held on holder 9 to be charged.

Next, a state of measurement device 1 according to this exemplary embodiment at the time of actual use will be described with reference to FIGS. 6 and 7.

As shown in FIG. 1, at the tinge of use of measurement device 1, the user holds the side portions at the center of measurement device 1 held on holder 9 between his/her fingers again, and then takes up measurement device 1 from holder 9 to convey measurement device 1 into container 10. As shown in FIG. 6, an axis in the longitudinal direction of measurement device 1 in which display unit 6 is directed upward is allowed to coincide with recesses 15 and 16 above container 10. Thereafter, container 10 is lowered so that scanner unit 5 enters accommodation chamber 13 and that sensor mounting section 4 is projected to an outside of accommodation chamber 12. Measurement device 1 is placed and held to coincide with recesses 15 and 16 holding measurement device 1.

A length of recess 15 is formed according to a shape of measurement device 1 at the other end side thereof (scanner unit 5 side). A length of recess 16 is shorter than the length of recess 15 according to the shape of measurement device 1 whose width is gradually decreased from the center thereof to the one end side thereof (sensor mounting section 4 side) in the longitudinal direction.

Therefore, measurement device 1 can be tightly held in an upper portion of accommodation chamber 12. Since the length of recess 16 is shorter than the length of recess 15, measurement device 1 cannot fall to an outside of container 10.

As a result, container 10 can be used as a holding container holding measurement device 1 in a state where sensor mounting section 4 of measurement device 1 is projected to the outside of accommodation chamber 12.

Figure 7:
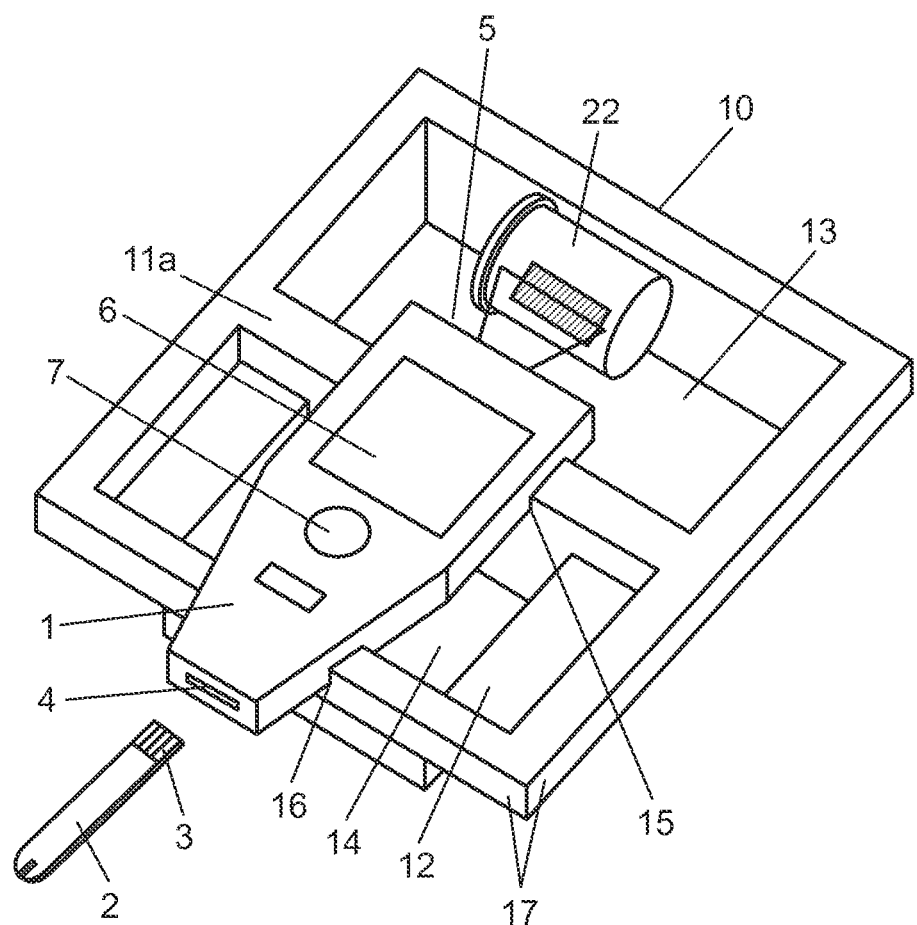
FIG. 7 is a perspective view of the container and the biological sample measurement device configuring the biological sample measurement apparatus according to the first exemplary embodiment of the present invention at the time of use.

Further, in this state, since measurement device 1 is held in recesses 15 and 16 in the upper portion of accommodation chamber 12, as shown in FIG. 7, scanner button 7 on the top surface of measurement device 1 can be pressed. Therefore, while bottle case (an example of medical use equipment) 22 is put in accommodation chamber 13. ID information thereof can be read by scanner unit 5 via a barcode. The biological sample measurement device can thus have high convenience.

Furthermore, in this state, since measurement device 1 is held in recesses 15 and 16 in the upper portion of accommodation chamber 12, measurement device 1 is located high to easily mount blood sugar level sensor 2 on sensor mounting section 4. The biological sample measurement device can thus have very high convenience.

When measurement device 1 is taken up again to measure a blood sugar level, the fingers to take up measurement device 1 can be inserted into a space of accommodation chamber 12 accommodating measurement device 1 therein at the time of conveyance and deep in recess 14 at the bottom thereof. Side surfaces of measurement device 1 can thus be tightly held. Measurement device 1 can thus be easily handled in busy hospital work.

As a result, container 10 can have high convenience.

As shown in FIG. 6, accommodation chamber 13 can accommodate therein other articles used at the time of measurement, e.g., medical use equipment, such as bottle case 22 accommodating blood sugar level sensor 2 (not shown) therein, needling instrument 23, a gauze (not shown), and a needle (not shown).

At the time of completion of blood sugar level measurement by measurement device 1, measurement device 1 is held in recesses 15 and 10 in the upper portion of accommodation chamber 12 to accommodate other articles used at the time of measurement in accommodation chamber 13. In this state, container 10 can be conveyed to the next measuring place by holding folding portion 17.

That is, container 10 can be used as a conveyance container which conveys measurement device 1 to the next measuring place, together with various articles necessary for measurement.

As a result, container 10 for packing used at the time of conveyance of measurement device 1 can be effectively used as the holding container and the conveyance container at the time of use of measurement device 1. The biological sample measurement device can thus have very high convenience.

As described above, the biological sample measurement device according to this exemplary embodiment includes container 10 having the opening in the top surface thereof and accommodation chambers 12 and 13 formed by separating the inner space and the opening in container 10 to right and left by partition wall 11a, measurement device 1 accommodated in accommodation chamber 12 of container 10, and holder 9 accommodated in accommodation chamber 13 of container 10 and holding the measure device.

In addition, recess 15 holding measurement device 1 is formed on the top surface of partition wall 11a, and recess 16 holding measurement device 1 is formed on the top surface of the outer peripheral wall of container 10 opposite to recess 15. The biological sample measurement device can thus have very high convenience.

That is, in the biological sample measurement device according to this exemplary embodiment, at the time of conveyance of measurement device 1, in a manufacturing factory, measurement device 1 and holder 9 are accommodated in container 10 having accommodation chambers 12 and 13 separated by partition wall 11a, and are integrated with container 10 to be conveyed to a conveyance destination (e.g., a hospital, and a home), and at the time of conveyance to a using place, container 10 can be used as the conveyance container for measurement device 1. The biological sample measurement device can thus have high convenience.

In addition, accommodation chamber 13 of container 10 can be used as an accommodation portion for other medical use equipment. In this respect, the biological sample measurement device can have high convenience.

Further, at the time of actual use of measurement device 1, the user takes up measurement device 1 from accommodation chamber 12, and can hold measurement device 1 in recesses 15 and 16 configuring the holding means holding measurement device 1 in a state where sensor mounting section 4 is projected to the outside of accommodation chamber 12. At the time of this use, the biological sample measurement device can have very high convenience.

Second Exemplary Embodiment

A biological sample measurement apparatus according to a second exemplary embodiment of the present invention will be described.

Figure 8:
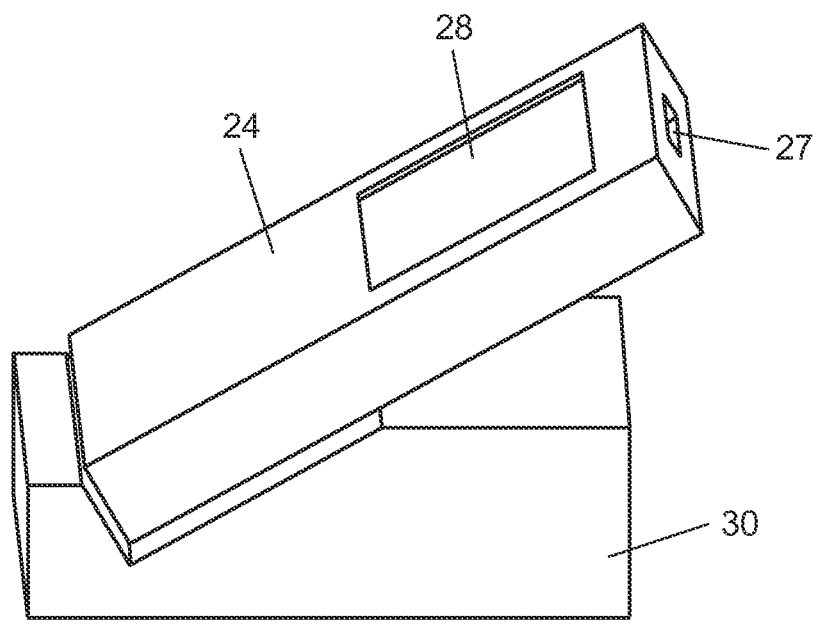
FIG. 8 is a perspective view of a biological sample measurement device and a holder configuring the biological sample measurement apparatus according to a second exemplary embodiment of the present invention.
Figure 9:
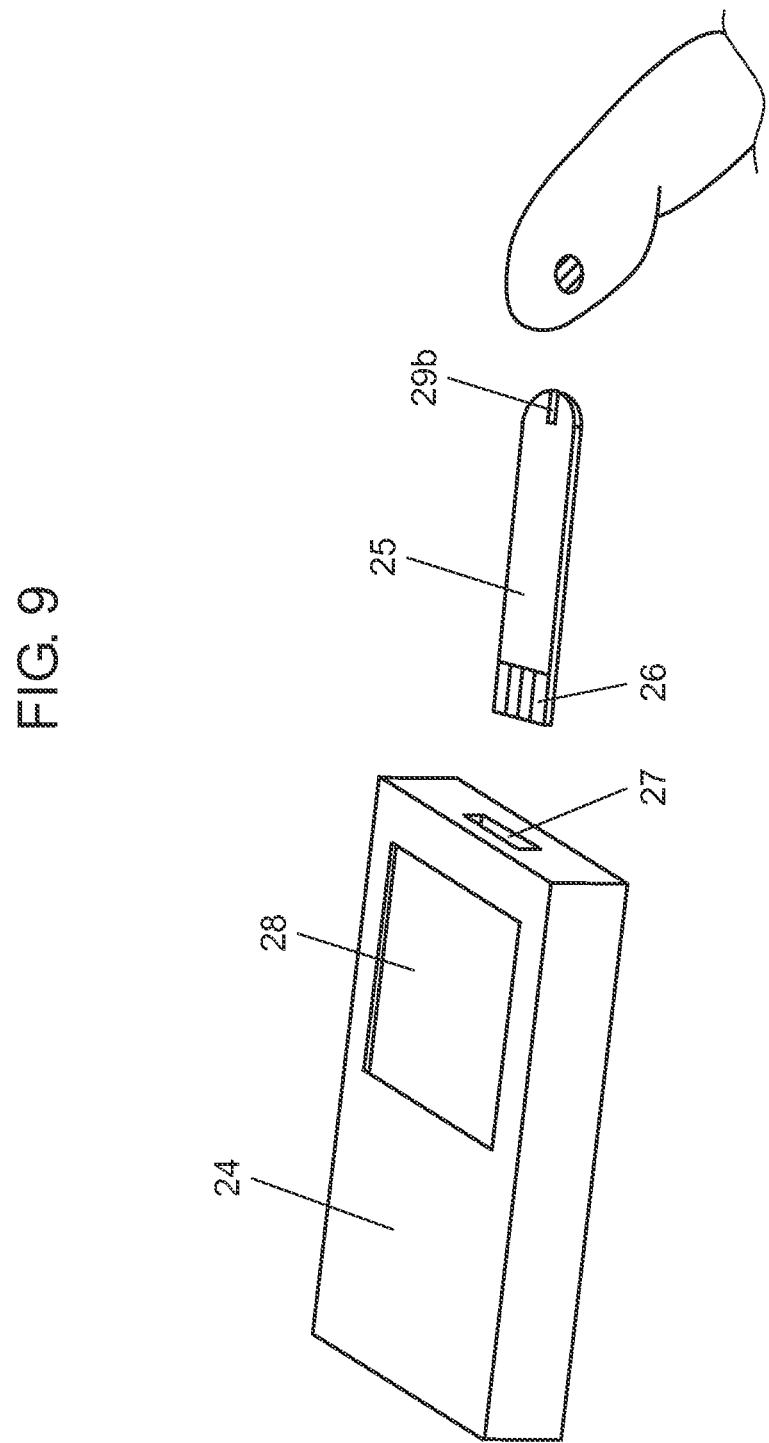
FIG. 9 is a perspective view of the biological sample measurement device configuring the biological sample measurement apparatus according to the second exemplary embodiment of the present invention at the time of use.

In FIG. 8, as shown in FIG. 9, sensor mounting section 27 is provided on an end side of blood sugar level measurement device 24 (an example of a biological sample measurement device), and inserts thereinto connection terminal 26 of blood sugar level sensor 25 (an example of a biological sample detection sensor). In addition, display unit 28 is provided on a top surface of measurement device 24.

That is, as shown in FIG. 9, connection terminal 26 at a rear of blood sugar level sensor 25 is mounted on sensor mounting section 27. In that state, blood is spotted onto spotting unit 29b at a front of blood sugar level sensor 25. A blood sugar level is then measured by a measurement unit (not shown) to be displayed on display unit 28.

Referring to FIG. 8 again, when not used, measurement device 24 is held on holder 30 to be charged.

Figure 10:
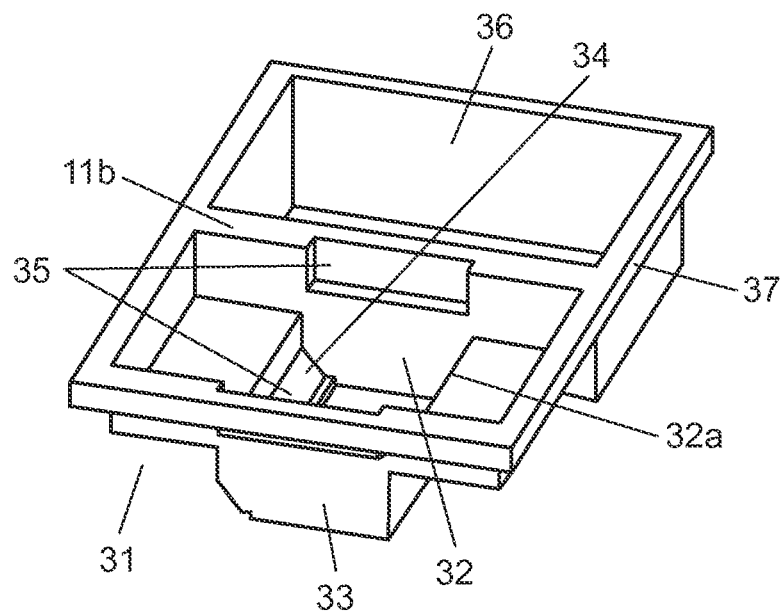
FIG. 10 is a perspective view of a container configuring the biological sample measurement device according to the second exemplary embodiment of the present invention, seen from above.

FIG. 10 is a diagram showing container 31 accommodating measurement device 24 and holder 30 therein.

Accommodation chamber (first accommodation chamber) 32 is provided from a center of container 31 to one side thereof (a lower side in FIG. 10), and accommodates measurement device 24 therein. Accommodation chamber 32 has a container shape so that a top surface thereof is rectangularly opened, and a rectangular parallelepiped space in an inner space thereof. In addition, a bottom at a center of accommodation chamber 32 is projected downward to form rectangular parallelepiped recess 33.

Figure 13:
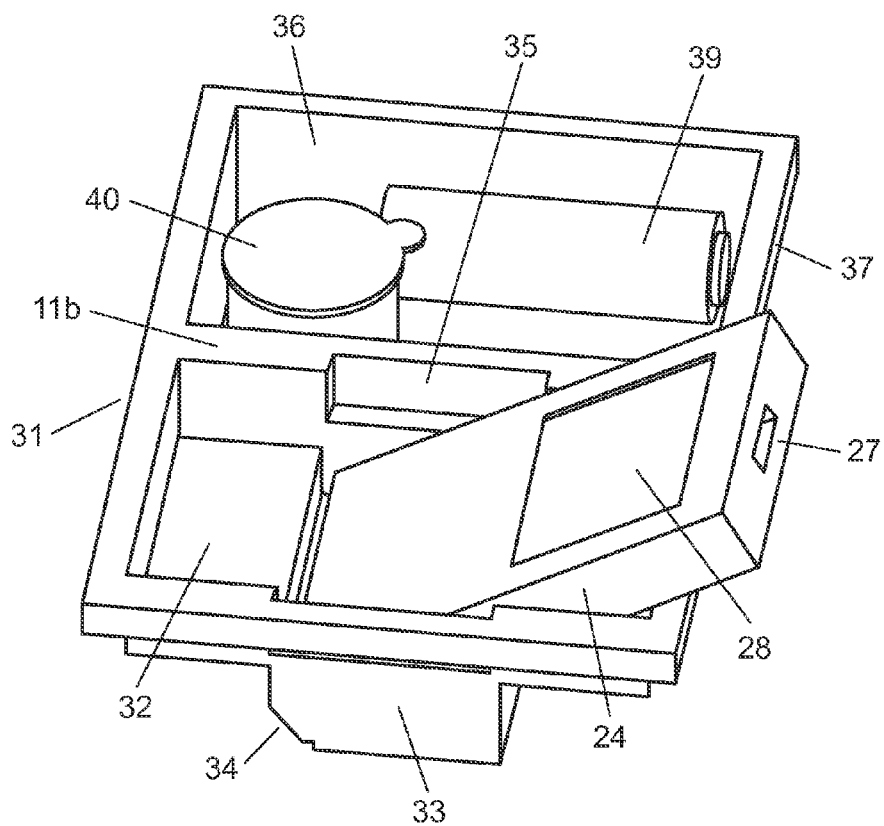
FIG. 13 is a perspective view of the container and the biological sample measurement device configuring the biological sample measurement apparatus according to the second exemplary embodiment of the present invention at the time of use.

Further, in this exemplary embodiment, holding portion 34 is provided on a lower side surface at a rear of recess 33 (a left side in FIG. 10), and configures holding means which tiltably holds measurement device 24 (shown in FIG. 13). Holding portion 34 has a tilted shape so that an upper side thereof is situated outside a lower side of recess 33.

Taking-out recesses 35 are provided in upper portions at centers of right and left long sides of accommodation chamber 32 having the rectangular opening, and are used for taking out measurement device 24.

Accommodation chamber (second accommodation chamber) 36 is provided from the center of container 31 to the other side thereof (an upper side in FIG. 10), and accommodates holder 30 therein. Like accommodation chamber 32, accommodation chamber 36 has a container shape so that a top surface thereof is rectangularly opened, and a rectangular parallelepiped space in an inner space thereof. Accommodation chambers 32 and 36 are formed by separating an inner space of container 31 and an opening in a top surface of container 31 by partition wall 11b.

Further, a bottom of accommodation chamber 36 is planar, and the bottom of accommodation chamber 36 and a bottom of recess 33 in accommodation chamber 32 are substantially flush with each other.

Figure 11:
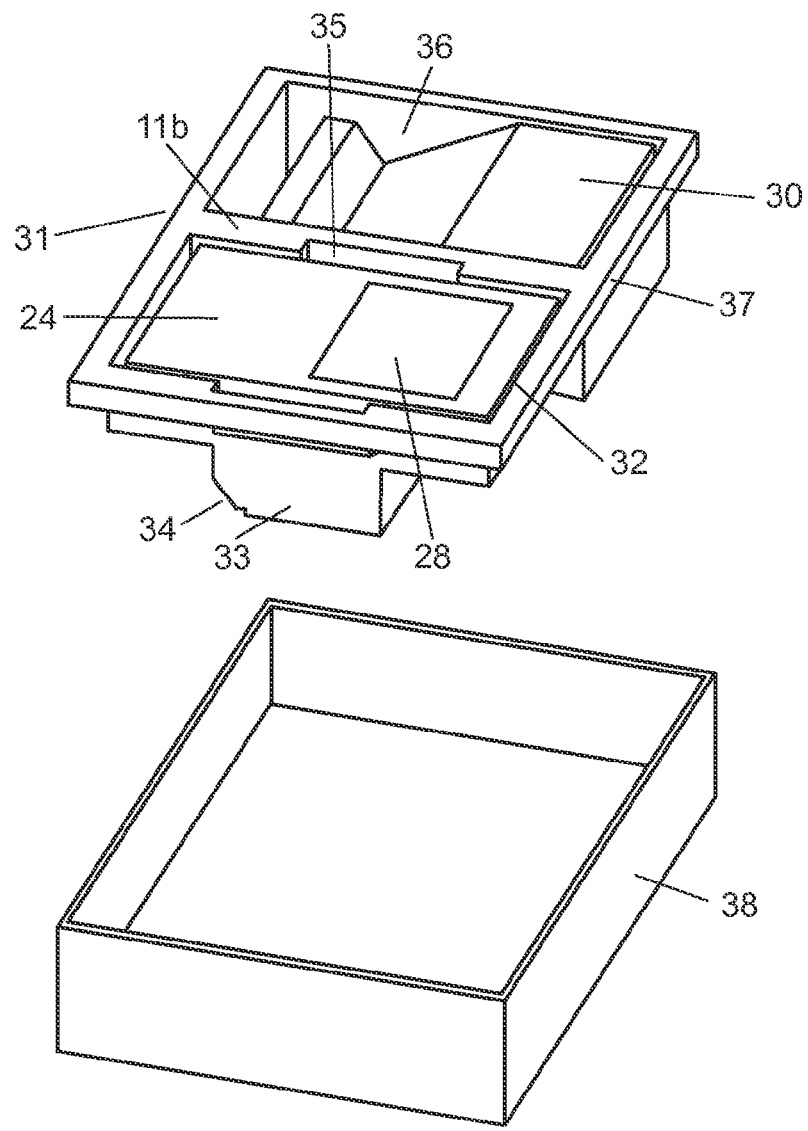
FIG. 11 is a perspective view of the biological sample measurement apparatus according to the second exemplary embodiment of the present invention at the time of conveyance.
Figure 12:
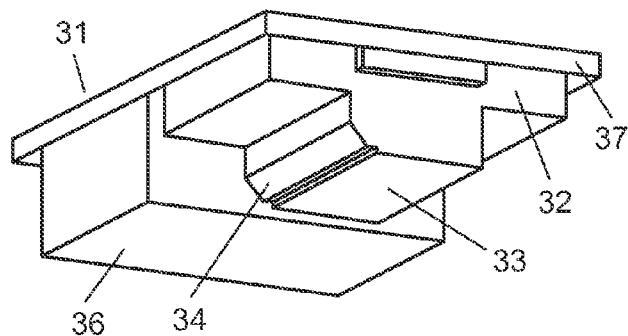
FIG. 12 is a perspective view of the container configuring the biological sample measurement apparatus according to the second exemplary embodiment of the present invention, seen from below.

In this exemplary embodiment, container 31 is formed of a resilient resin (e.g., polypropylene). As shown in FIGS. 10 to 12, folding portion 37 is provided on an overall periphery of the top surface of container 31 so that ends thereof are folded downward. An outer peripheral strength of container 31 can thus be enhanced. Therefore, container 31 can be conveyed by holding folding portion 37.

In the above configuration, features of the biological sample measurement apparatus according to this exemplary embodiment will be described below with reference to FIGS. 11 to 13.

FIG. 11 is a diagram showing a state according to this exemplary embodiment at the time of conveyance. As shown in FIG. 11, in a manufacturing factory, measurement device 24 is accommodated in accommodation chamber 32 of container 31, and holder 30 is accommodated in accommodation chamber 36 of container 31. Thereafter, measurement device 24 and holder 30 integrated with container 31 are accommodated and packed in box 38 to be conveyed to a conveyance destination (e.g., a hospital, and a home).

As described above, recess 33 at the bottom of accommodation chamber 32 is formed of a resilient resin (e.g., polypropylene). Vibration with respect to measurement device 24 at the time of conveyance can thus be effectively prevented.

FIG. 12 is a diagram of container 31, seen from a lower surface thereof. As described above, in FIG. 12, the bottom of accommodation chamber 36 and the bottom of recess 33 in accommodation chamber 32 are substantially flush with each other. Therefore, at the time of conveyance, the bottoms are abutted onto a bottom of box 38 in FIG. 11. In addition, folding portion 37 on the overall outer periphery in an upper portion of container 31 is abutted onto an upper portion of box 38. Container 31 can thus be conveyed to be tightly held in box 38.

FIG. 11 shows only box 38 in which an upper surface thereof is opened, but, of course, a box in which a lower surface thereof is opened (not shown) covers an outer periphery of box 38 from above. Upper and lower boxes 38 thus cover container 31.

That is, container 31 can be used as a conveying material at the time of conveyance.

When container 31 reaches a conveyance destination (e.g., a hospital, and a home), container 31 is taken out from box 38, and holder 30 is then taken out from container 31 to be installed in an e.g. appropriate charging place. Thereafter, measurement device 24 is taken out from container 31. As shown in FIG. 8, measurement device 24 is held on holder 30 to be charged.

As shown in FIG. 13, charged measurement device 24 is installed in accommodation chamber 32. That is, FIG. 13 is a diagram showing a state of measurement device 24 according to this exemplary embodiment at the time of actual use.

Container 31 can be used as a holding container which tiltably holds measurement device 24 in accommodation chamber 32. Specifically, a rear end surface of measurement device 24 in which display unit 28 is directed upward is inserted from the opening in the top surface of accommodation chamber 32, and as shown in FIG. 13, is abutted onto the tilted surface of holding portion 34 on the side surface of recess 33 in accommodation chamber 32. Then, the rear end surface of measurement device 4 is held on the tilted surface of holding portion 34. A center in a lower portion of measurement device 24 is held on upper side 32a (shown in FIG. 10) opposite to the tilted surface of recess 33. As shown in FIG. 13, measurement device 24 is tiltably stably held in accommodation chamber 32. Sensor mounting section 27 of measurement device 24 is projected to an outside of accommodation chamber 32.

As shown in FIG. 13, in this state, in measurement device 24, sensor mounting section 27 of blood sugar level sensor 25 (shown in FIG. 9) is directed upward. Blood sugar level sensor 25 can thus be easily mounted on sensor mounting section 27. The biological sample measurement device can thus have very high convenience.

That is, at the time of actual use of measurement device 24, container 31 can be used as the holding container for measurement device 24.

In addition, accommodation chamber 36 can accommodate therein other articles used at the time of measurement, e.g., needling instrument 39, bottle case 40 accommodating blood sugar level sensor 25 (not shown) therein, a gauze (not shown), and a needle (not shown).

At the time of completion of blood sugar level measurement by measurement device 24, measurement device 24 is horizontally accommodated in accommodation chamber 32 (shown in FIG. 11). In this state, container 31 can be conveyed to the next measuring place by holding folding portion 37.

That is, container 31 can be used as a conveyance container which conveys measurement device 24 to a measuring place, together with various articles necessary for measurement.

As a result, container 31 for packing used at the time of conveyance of measurement device 24 can be effectively used as the holding container and the conveyance container at the time of use of measurement device 24. The biological sample measurement device can thus have very high convenience.

As shown in FIG. 10, in this exemplary embodiment, holding portion 34 configuring the holding means is formed of the tilted surface. However, in place of the tilted surface, holding portion 34 may be configured of a plane parallel to the bottom of recess 33 (in this state, the bottom of recess 33 and holding portion 34 are step-like). In this configuration, accommodation chamber 32 of container 31 can be used as the holding container which erectably holds measurement device 24.

Specifically the rear end surface of measurement device 24 is abutted onto the plane of holding portion 34 from above. Then, measurement device 24 is erectably held in holding portion 34.

In the holding state, sensor mounting section 27 of blood sugar level sensor 25 is directed upward. Blood sugar level sensor 25 can be easily mounted on sensor mounting section 27. The biological sample measurement device can thus have very high convenience.

As shown in FIG. 12, in this exemplary embodiment, holding portion 34 of recess 33 is provided upward of the bottom of recess 33. Therefore, as shown in FIG. 13, even, when measurement device 24 is inserted into recess 33 in accommodation chamber 32 to abut the rear end surface of measurement device 24 onto holding portion 34, the rear end surface of measurement device 24 cannot come into collision onto the bottom of recess 33, that is, onto a ground plane of container 31. Measurement device 24 which is a precision machine can thus be protected.

As described above, in this exemplary embodiment, measurement device 24, holder 30 holding measurement device 24, and container 31 having accommodation chambers 32 and 36 for the biological sample measurement device are included. In addition, holding portion 34 is formed in accommodation chamber 32 of container 31, and configures the holding means which holds measurement device 24 in a tilted or upright position. The biological sample measurement device can thus have very high convenience.

That is, in this exemplary embodiment, at the time of conveyance of measurement device 24, in a manufacturing factory, measurement device 24 is accommodated in accommodation chamber 32 of container 31, holder 30 is accommodated in accommodation chamber 36 of container 31, and measurement device 24 and holder 30 are integrally packed in container 31 to be conveyed to a conveyance destination (e.g., a hospital, and a home). That is, container 31 can be used as an article to be conveyed for conveyance.

On the other hand, at the time of actual use (measurement) of measurement device 24, measurement device 24 in a tilted or upright position can be held on holding portion 34 in accommodation chamber 32 of container 31 in a state where sensor mounting section 27 is projected to the outside of accommodation chamber 32. That is, container 31 can be used as the holding container for measurement device 24.

As a result, the article to be conveyed used at the time of conveyance can be effectively used as the holding container at the time of use of measurement device 24. The biological sample measurement device can thus have very high convenience.

Third Exemplary Embodiment

Figure 14:
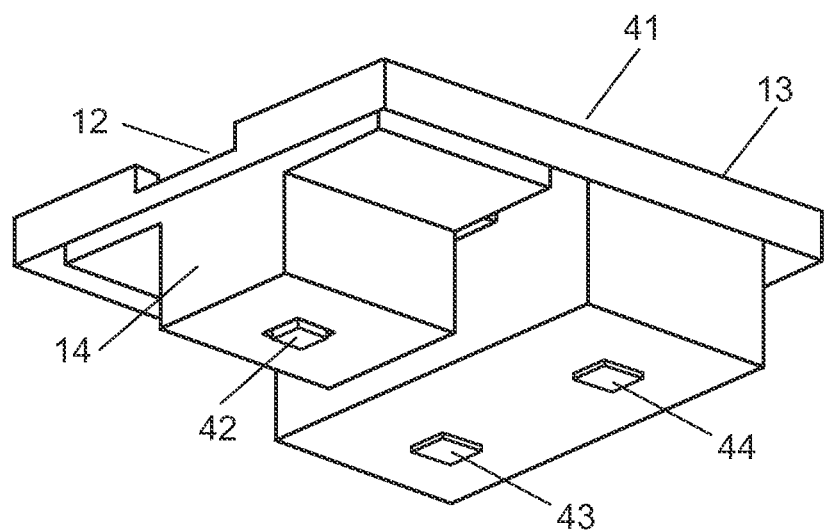
FIG. 14 is a perspective view of a container configuring a biological sample measurement apparatus according to a third exemplary embodiment of the present invention, seen from a lower surface thereof.

FIG. 14 is a perspective view of container 41 of a biological sample measurement apparatus according to a third exemplary embodiment of the present invention, seen from a lower side thereof.

In container 41, rotation shaft 42 is provided in container 10 of the first exemplary embodiment, and is projected downward from an outer surface at the bottom of accommodation chamber 12 of container 10.

Rotation shaft 42 is formed of a rectangular parallelepiped rubber (an example of an elastic body). The rectangular parallelepiped rubber adheres onto the outer surface at the bottom at a center of accommodation chamber 12 with a double-faced tape (the double-faced tape is not present on a bottom surface of the rubber, so that the surface of the rubber is exposed).

Supporting portion 43 (first supporting portion) and supporting portion 44 (second supporting portion) are formed at the bottom of accommodation chamber 13 of container 41, and are integrally pushed and projected downward from the bottom of accommodation chamber 13 of container 41.

Rotation shaft 42 and supporting portions 43 and 44 have substantially the same downward projection height. As seen from FIG. 14, rotation shaft 42 and supporting portions 43 and 44 form an isosceles triangle in which rotation shaft 42 is an apex thereof. Container 41 can thus be stably held.

Figure 15:
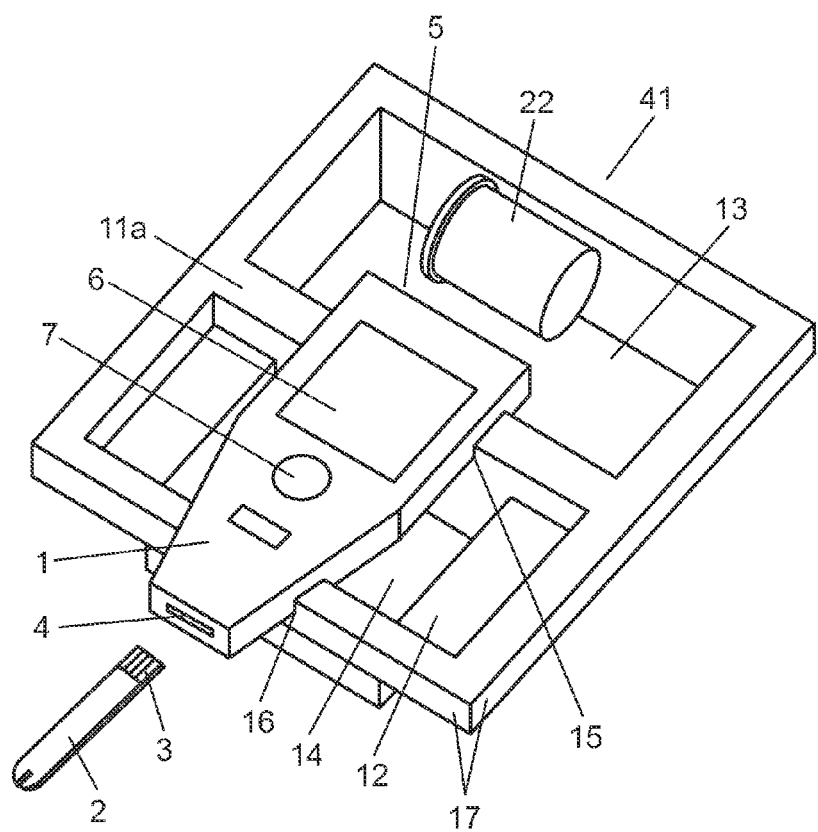
FIG. 15 is a perspective view of the container and the biological sample measurement device configuring the biological sample measurement apparatus according to the third exemplary embodiment of the present invention at the time of use.

As shown in FIG. 15, for instance, a measuring person holds measurement device 1 in recesses 15 and 16 configuring the holding means in the upper portion of accommodation chamber 12 of container 41, places container 41 on a wagon (not shown) in a state where other articles (e.g., bottle case 22) used at the time of measurement are accommodated in accommodation chamber 13, and conveys measurement device 1 to the next measuring place.

That is, like container 10 according to the first exemplary embodiment, as shown in FIG. 15, container 41 can be used at the time of actual use as a holding container holding measurement device 1 in a state where sensor mounting section 4 of measurement device 1 is projected to the outside of accommodation chamber 12.

As described above, in container 41 according to this exemplary embodiment, rotation shaft 42 is provided in the outer surface at the bottom of accommodation chamber 12, so that container 41 is rotatable in a horizontal direction about rotation shaft 42. More specifically, the rubber forming rotation shaft 42 of container 41 is tightly abutted onto a top surface of the wagon placing container 10 thereon to form the rotation shaft of container 41. About rotation shaft 42 of container 41, supporting portions 43 and 44 formed of a resin are slid on the top surface of the wagon to rotate container 41. That is, since as described above, the surface of the rubber is exposed, rotation shaft 42 has high friction resistance, and since supporting portions 43 and 44 are integrated with container 10 with a resin have low friction resistance. Therefore, about rotation shaft 42, resin supporting portions 43 and 44 are slid on the top surface of the wagon. Container 41 can thus be easily rotated.

As described above, since measurement device 1 is held in recesses 15 and 16 in the upper portion of accommodation chamber 12 of container 41 in a state where sensor mounting section 4 of measurement device 1 is projected to the outside of accommodation chamber 12, a weight of measurement device 1 is applied to rotation shaft 42 at the bottom of accommodation chamber 12 so that the rotation center of container 41 being rotated is stable. As a result, container 41 can be easily rotated.

That is, as shown in FIG. 15, for instance, the measuring person inserts the fingers of his/her right hand into accommodation chamber 13 in a state where sensor mounting section 4 of measurement device 1 is directed toward the measuring person to push an inner wall surface of accommodation chamber 13 with the fingers of his/her right hand for rotating container 41 clockwise. Then, container 41 is rotated about rotation shaft 42 to slide supporting portions 43 and 44 on the ground plane, so that container 41 can be easily rotated in the horizontal direction.

Therefore, the measuring person can easily bring bottle case 22 in accommodation chamber 13 on the opposite side of the measuring person toward the measuring person, and can easily take out bottle case 22.

As a result, the biological sample measurement device can have very high convenience in e.g., busy hospital work.

In this exemplary embodiment, rotation shaft 42 is formed of a black rubber (an example of an elastic body), and supporting portions 43 and 44 are formed of a transparent or semitransparent resin (e.g., polypropylene). In this manner, since rotation shaft 42 and supporting portions 43 and 44 have different colors, the measuring person can clearly identify rotation shaft 42.

Further, as described above, rotation shaft 42 and supporting portions 43 and 44 form an isosceles triangle in which rotation shaft 42 is an apex thereof. Container 41 can thus be stably supportably rotated.

Rotation shaft 42 is provided at the bottom of accommodation chamber 12 holding heavy measurement device 1. The weight of measurement device 1 is supported at rotation shaft 42 underneath measurement device 1 to tightly abut rotation shaft 42 onto the top surface of the wagon by the weight of measurement device 1. About rotation shaft 42, container 41 can thus be stably rotated in the horizontal direction.

As a result, an article to be conveyed used at the time of conveyance can be effectively used as the holding container at the time of use of measurement device 1. The biological sample measurement device can thus have very high convenience.

As described above, the biological sample measurement apparatus of the present invention includes the container having the opening in the top surface thereof and the first and second accommodation chambers formed by separating the inner space and the opening in the container to right and left by the partition wall, the biological sample measurement device accommodated in the first accommodation chamber of the container, and the holder accommodated in the second accommodation chamber of the container for holding the biological sample measurement device. The biological sample measurement apparatus further includes the holding means holding the biological sample measurement device on the outer peripheral wall configuring the first accommodation chamber or in the first accommodation chamber in a state where the sensor mounting section of the biological sample measurement device is projected to the outside of the first accommodation chamber. In addition, the rotation shaft is projected downward from the bottom of the first accommodation chamber. The biological sample measurement device can thus have very high convenience.

That is, in the present invention, at the time of conveyance of the biological sample measurement device, in a manufacturing factory, the biological sample measurement device and the holder are accommodated in the container having the first and second accommodation chambers separated by the partition wall, and are integrated with the container to be conveyed to a conveyance destination (e.g., a hospital, and a home). At the time of conveyance to a using place, the container can be used as the conveyance container for the biological sample measurement device. The biological sample measurement device can thus have high convenience.

In addition, the second accommodation chamber of the container can also be used as the accommodation portion for other medical use equipment. In this respect, the biological sample measurement device can have high convenience. That is, at the time of actual use, the holder is taken out from the second accommodation chamber of the container, so that at the time of actual use, the second accommodation chamber of the container can also be used as the accommodation portion for other medical use equipment. In this respect, the biological sample measurement device can have high convenience.

Further, the container includes the holding means holding the biological sample measurement device in a state where the sensor mounting section projected to the outside of the first accommodation chamber after the biological sample measurement device is taken up from the first accommodation chamber by the user in a using place. Therefore, the container can be used as an installing portion for embodying the biological sample measurement device. At the time of actual use, the biological sample measurement device can have very high convenience.

Furthermore, in the present invention, the rotation shaft is projected downward from the bottom of the first accommodation chamber. Since the biological sample measurement device is held on the holding means in a state where the sensor mounting section of the biological sample measurement device is projected to the outside of the first accommodation chamber, the container can be easily rotated so that the user can easily perform an operation. In this respect, the biological sample measurement device can have very high convenience.

This point will be briefly specifically described now. Since the rotation shaft is projected downward from the bottom of the first accommodation chamber, when the user rotates the container in a direction so that the user can easily perform an operation, the container can be easily rotated about the rotation shaft. An operability of the operator thus becomes very high. In this respect, the biological sample measurement device can have high convenience.

INDUSTRIAL APPLICABILITY

The present invention can provide the biological sample measurement device having very high convenience at the time of packing at manufacturing, at the time of conveyance to a conveyance destination after packing, at the time of conveyance until actual use after unpacking at the conveyance destination, at the time of actual use, and at the time of conveyance after actual use.

REFERENCE MARKS IN THE DRAWINGS 1, 24 measurement device (an example of a biological sample measurement device)
2, 25 blood sugar level sensor (an example of a biological sample detection sensor)
3, 26 connection terminal
4, 27 sensor mounting section
5 scanner unit (an example of an optical information reading unit)
6, 28 display unit
7 scanner button
8 power source button
9, 30 holder
9a holding portion
9b stopper
10, 31, 41 container
11a, 11b partition wall
12, 13, 32, 36 accommodation chamber
14, 33 recess
15, 16, 35 recess
17, 37 folding portion
18 measurement unit.
19 control unit
20 power source
21, 38 box 22, 40 bottle case
23, 39 needling instrument
29a, 29b spotting portion
34 holding portion
42 rotation shaft
43, 44 supporting portion

The invention claimed is:

1. A biological sample measurement apparatus comprising:
- a container having an opening in a top surface thereof and first and second accommodation chambers;
- a partition wall that separates an inner space of the container and the opening into the first and the second accommodation chambers;
- a biological sample measurement device accommodated in the first accommodation chamber;
- a holder accommodated in the second accommodation chamber and configured to hold the biological sample measurement device; and
- a holding section provided on an outer peripheral wall of the first accommodation chamber and including a first recess and a second recess, the holding section being configured to hold the biological sample measurement device with a sensor mounting section of the biological sample measurement device jutting out of the first accommodation chamber,
- wherein the first recess is provided in a top surface of the partition wall and configured to hold the biological sample measurement device, and the second recess is provided in a top surface of an outer peripheral wall of the container and configured to hold the biological sample measurement device, the second recess being opposite to the first recess.

2. The biological sample measurement apparatus according to claim 1, wherein the second recess is formed on a top surface of the outer peripheral wall of the first accommodation chamber.

3. The biological sample measurement apparatus according to claim 2, wherein a length of the second recess is shorter than a length of the first recess.

4. The biological sample measurement apparatus according to claim 3, wherein the biological sample measurement device has a substantially rectangular parallelepiped shape, one end side thereof is a biological sample measurement side, the other end side thereof is an information reading side, and a width at the one end side orthogonal to a longitudinal direction of the biological sample measurement device is smaller than a width at the other end side orthogonal to the longitudinal direction.

5. The biological sample measurement apparatus according to claim 4, wherein the sensor mounting section for a biological sample detection sensor is provided on the one end side of the biological sample measurement device.

6. The biological sample measurement apparatus according to claim 5, wherein an optical information reading unit is provided on the other end side of the biological sample measurement device.

7. The biological sample measurement apparatus according to claim 1, wherein a bottom of the first accommodation chamber and a bottom of the second accommodation chamber are flush with each other.

8. The biological sample measurement apparatus according to claim 1, wherein a rotation shaft is provided at a bottom of the first accommodation chamber, the rotation shaft projecting downward from the bottom of the first accommodation chamber.

9. The biological sample measurement apparatus according to claim 8, wherein, the rotation shaft is formed of an elastic body and is adhered to an outer surface at the bottom of the first accommodation chamber.

10. The biological sample measurement apparatus according to claim 9, wherein a bottom of the second accommodation chamber is provided with a first supporting portion and a second supporting portion projecting downward from the bottom of the second accommodation chamber, and the first supporting portion, the second supporting portion, and the rotation shaft are arranged to hold the container.

11. The biological sample measurement apparatus according to claim 10, wherein the rotation shaft, the first supporting portion, and the second supporting portion have substantially equal projection height.

12. The biological sample measurement apparatus according to claim 11, wherein the rotation shaft has a color different from colors of the first supporting portion and the second supporting portion.

13. The biological sample measurement apparatus according to claim 12, wherein the rotation shaft is black, and the first supporting portion and the second supporting portion are transparent or semitransparent.

* * * * *